United States Patent [19]

Selick

[11] Patent Number: 5,348,358
[45] Date of Patent: Sep. 20, 1994

[54] CONTACT LENS INSERTION TOOL

[76] Inventor: David A. Selick, 76 Leroy St., Tenafly, N.J. 07670

[21] Appl. No.: 20,796

[22] Filed: Feb. 22, 1993

[51] Int. Cl.⁵ .............................................. A61F 9/00
[52] U.S. Cl. ........................................ 294/1.2; 294/902
[58] Field of Search .................... 294/1.1, 1.2, 902; 606/107

[56] References Cited

U.S. PATENT DOCUMENTS

| | | |
|---|---|---|
| 3,411,364 | 11/1968 | Horloy et al. . |
| 3,879,076 | 4/1975 | Barnett . |
| 4,047,532 | 9/1977 | Phillips et al. ............... 606/107 |
| 4,088,359 | 5/1978 | Buchanan . |
| 4,126,345 | 11/1978 | List ................................ 294/1.2 |
| 4,167,283 | 9/1979 | Feldman . |
| 4,190,277 | 2/1980 | England . |
| 4,192,204 | 3/1980 | Feldman . |
| 4,200,320 | 4/1980 | Durham . |
| 4,245,859 | 1/1981 | Rainin ........................... 294/1.2 |
| 4,479,672 | 10/1984 | Jermyn . |
| 4,512,601 | 4/1985 | Jacobstein . |
| 4,512,602 | 4/1985 | England . |
| 4,753,470 | 6/1988 | Monard . |
| 4,763,650 | 8/1988 | Hauser . |
| 4,964,663 | 10/1990 | Jermyn . |
| 4,986,586 | 1/1991 | Ellrich et al. . |

FOREIGN PATENT DOCUMENTS 1431168  4/1976  United Kingdom ............... 294/1.2

Primary Examiner—Dean J. Kramer
Attorney, Agent, or Firm—Gottlieb, Rackman & Reisman

[57] ABSTRACT

A contact lens insertion tool and a method of implementing the same wherein the tool comprises an elongated handle section having a top surface, a bottom surface, and two side surfaces; an intermediate section angularly displaced from the handle section at an acute angle; and a lens supporting section angularly displaced from the intermediate section at a second acute angle that is greater than the first acute angle, and further including a substantially circular cross sectional land area for engaging a contact lens. The novel contact lens insertion tool is first grasped by a user who will then manipulate the tool to adhere the contact lens to the land area by means of the adhesion between the lens and the land area. Next, the user will bring the contact lens edge first to the bottom central area of the sclera of the eye into which insertion is desired, and will secure contact between the lens edge and the eye at an angle ranging from approximately 20° to not greater than 90°. Finally, the user will rotate the tool upward until a point where the adhesion between the contact lens and the eye exceeds the adhesion between the contact lens and the land area of the contact lens insertion tool, thus disposing the contact lens in the user's eye.

22 Claims, 6 Drawing Sheets

CONTACT LENS INSERTION TOOL

TECHNICAL FIELD

The invention relates to the insertion and positioning of contact lenses, and more particularly to a tool and method for inserting a contact lens into a user's eye with a minimal degree of effort, discomfort, and risk of contamination to the lens.

BACKGROUND ART

For aesthetic reasons and because of their increased effectiveness compared to glasses, contact lenses enjoy a substantial portion of the market for corrective lenses. Unfortunately, for a great many contact lens users, the insertion of the lens into the eye can require a great deal of effort and can cause significant discomfort. Furthermore, the risk of contamination to the lens is very great during insertion.

Heretofore, there have been many different types of contact lens applicators to facilitate insertion and removal of the lens from one's eye. Examples of such prior art devices can be found in U.S. Pat. Nos. 3,879,076; 4,088,359; and 4,167,283. These prior art instruments have not been met with great success because of their complicated arrangements and awkward designs which often result in impeding the vision of a contact lens wearer during insertion.

Accordingly, it is a primary object of the present invention to provide a new and improved contact lens insertion tool and method.

Furthermore, it is an object of the present invention to provide a contact lens insertion tool and method which minimizes discomfort during insertion of a contact lens.

It is another object of the present invention to provide a contact lens insertion tool and a contact lens insertion method which requires a minimal amount of time and effort for insertion of the contact lens.

It is still a further object of the present invention to provide a contact lens insertion tool and a contact lens insertion method which mimimizes the risk of contamination due to unsanitary contact with the lens.

It is yet another object of the present invention to provide a contact lens insertion tool and a contact lens insertion method which substantially reduces blinking during insertion and positioning of a contact lens.

It is a further object of the present invention to provide a contact lens insertion tool made of an integral unit to decrease production costs and to minimize the risk of breakage.

Further objects and advantages of this invention will become apparent as the following description proceeds.

SUMMARY OF THE INVENTION

Briefly stated, and in accordance with one embodiment of this invention, a contact lens insertion device and a method for implementing the same, which minimizes discomfort, effort, and risk of contamination is described.

The novel contact lens insertion tool described herein comprises (i) an elongated handle section having a top surface, a bottom surface, and two side surfaces; (ii) an intermediate section angularly displaced from the handle section at an obtuse angle; and (iii) a lens supporting portion angularly displaced from the intermediate section at a different obtuse angle that is greater than the first obtuse angle, and having a substantially circular cross sectional land area for engaging the contact lens.

The design of the contact lens insertion tool minimizes the need to blink, which complicates insertion and proper positioning of a lens. The land area may be smooth or texturized (roughened) and flat, convex, or concave depending upon the desired degree of adhesiveness between the lens and the land area. A faceted ball configuration, emanating from and integral to the lens supporting section of the contact lens insertion tool, provides a multi-land area device suitable for picking up and maneuvering a contact lens. Each facet or land area of said faceted ball construction can be smooth, texturized (roughened), concave, convex, or any combination of the foregoing as desired.

The novel design of the contact lens insertion tool permits an advantageous method of inserting the lens into a user's eye. The user will: (i) grasp the handle section of the tool; (ii) engage the contact lens to the land area of the tool by means of the adhesion between the lens, and/or the lens fluid bathing the lens, and the land area; (iii) bring the contact lens, edge first, to the bottom central sclera area of the eye in which insertion is desired to secure contact between the lens edge and the eye at any acute angle from approximately 20° to not greater than 90° as is found to be comfortable, and in such a manner that the tool does not impede the user's vision; and (iv) rotating the tool upward and toward the eye to an angular position where the adhesion between the contact lens and the eye exceeds the adhesion between the contact lens and the land area of the tool whereby the contact lens is disposed in the user's eye. Preferably, the user will gently pull down on the cheek directly beneath the lower eyelid of the eye which is to receive the contact lens, in order to expose a greater area of the lower sclera portion of the eye, thus facilitating insertion of the contact lens. Finally, in the event that the contact lens is not properly positioned over the cornea of the eye during the insertion step, the novel tool can be used to gently nudge the contact lens into its correct position.

BRIEF DESCRIPTION OF THE DRAWINGS

While the specification concludes with claims particularly pointing out and distinctly claiming the subject matter regarded as the invention herein, it is believed that the present invention will be more readily understood from the following detailed description, taken in conjunction with the accompanying drawings, in which:

DETAILED DESCRIPTION OF THE PREFERRED EMBODIMENT

Figure 1:
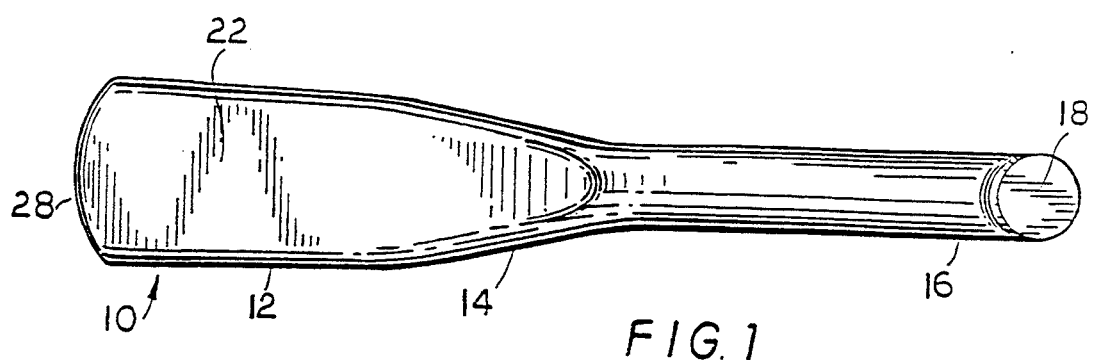
FIG. 1 is a top view illustrating a preferred embodiment of the contact lens insertion tool in accordance with the present invention.
Figure 2:
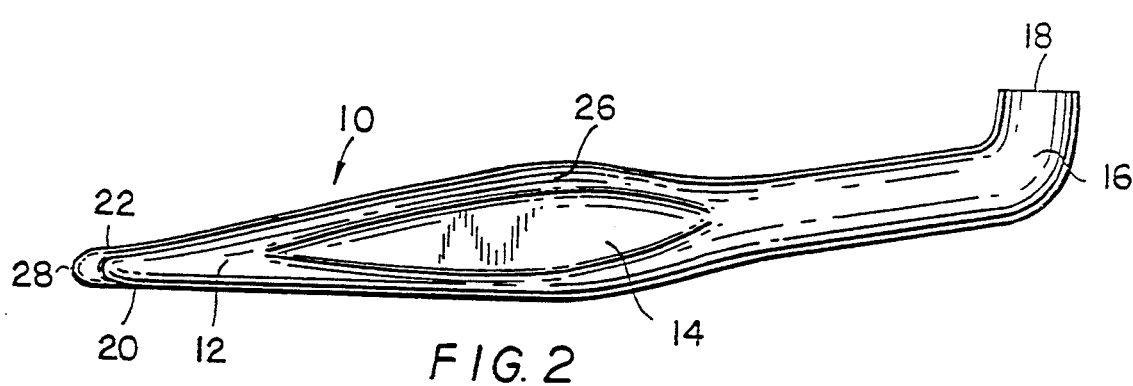
FIG. 2 is a side view of the contact lens insertion tool illustrated in FIG. 1.

Referring to FIG. 1, a top view of the contact lens insertion tool, generally designated 10, is shown. FIG. 2 illustrates a side view of contact lens insertion tool 10. It should be noted that in a preferred embodiment of the present invention, the top and bottom surfaces and the two side surfaces of the contact lens insertion tool 10 are opposingly symmetric.

Figure 7:
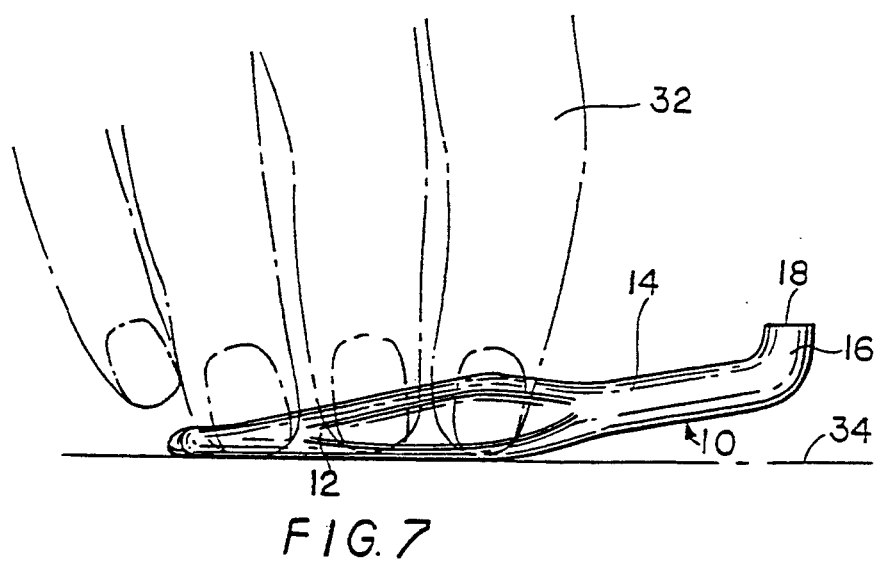
FIG. 7 is a perspective view of a user's hand grasping the contact lens insertion tool in accordance with the method of the present invention.

As best seen in FIGS. i and 2, contact lens insertion tool 10 is comprised of handle section 12, intermediate section 14, and lens supporting section 16. Handle section 12 comprises wide and flat bottom surface 20 and top surface 22. As can be seen in FIG. 7, flat bottom surface 20 permits the contact lens insertion tool 10 to lie freely in an upright position. This prevents land area 18, which will come in direct contact with lens 40, from touching surfaces which may contain bacteria, dust, or other contaminants and irritants.

Intermediate section 14 is angularly displaced at an obtuse angle from handle section 12. Handle section 12 has side surfaces 26 which widen as it moves away from proximal end 28. At the same length of tool 10 where side surfaces are widened, top surface 22 and bottom surface 20 are correspondingly tapered. Lens supporting section 16 terminates at a distal end with a generally circular cross sectional land area 18. Land area 18 will be used to pick up and maneuver contact lens 40.

Figure 3:
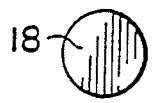
FIG. 3 is a top view of a smooth land area of the novel contact lens insertion tool.
Figure 4:
FIG. 4 is a top view of a texturized (roughened) land area of the contact lens insertion tool of the present invention.
Figure 5:
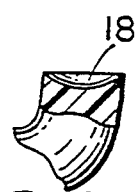
FIG. 5 is a side view of a concave land area for the contact lens insertion tool in accordance with the present invention.
Figure 6:
FIG. 6 is a side view of the convex land area for the contact lens insertion tool in accordance with the present invention.

Land area 18 can take on various shapes and its surface can be modified depending upon the degree of adhesiveness desired. Land area 18 can comprise a smooth surface such as indicated in FIG. 3 or a texturized (toughened) surface as indicated in FIG. 4. The texturized (roughened) surface of land area 18 in FIG. 4, will provide a relatively lesser degree of adhesiveness based on adhesion with contact lens 40, than will the smooth land area 18 of FIG. 3. Moreover, land area 18 can be flat as indicated in FIG. 2, concave as indicated in FIG. 5, or convex as indicated in FIG. 6. In either embodiment, it is important that there are no sharp edges on the land area 18 which could possibly damage lens 40 or injure the user's eye.

The degree of the concave angle in FIG. 5 should be designed to correspond generally to the degree of curvature of lens 40 thereby forming a greater adhesive contact region. The convex embodiment of FIG. 6 allows for greater maneuverability of lens 40 on land area 18, but also results in a smaller adhesive region.

The acute angle between intermediate section 14 and elongated handle section 12, and the second acute angle between lens supporting section 16 and intermediate section 14, together combine, in the preferred embodiment of the present invention, to form a total angular displacement of approximately 90° between lens supporting section 16 and handle section 12. This design permits easy use of the inventive apparatus as will be described herein.

Figure 8:
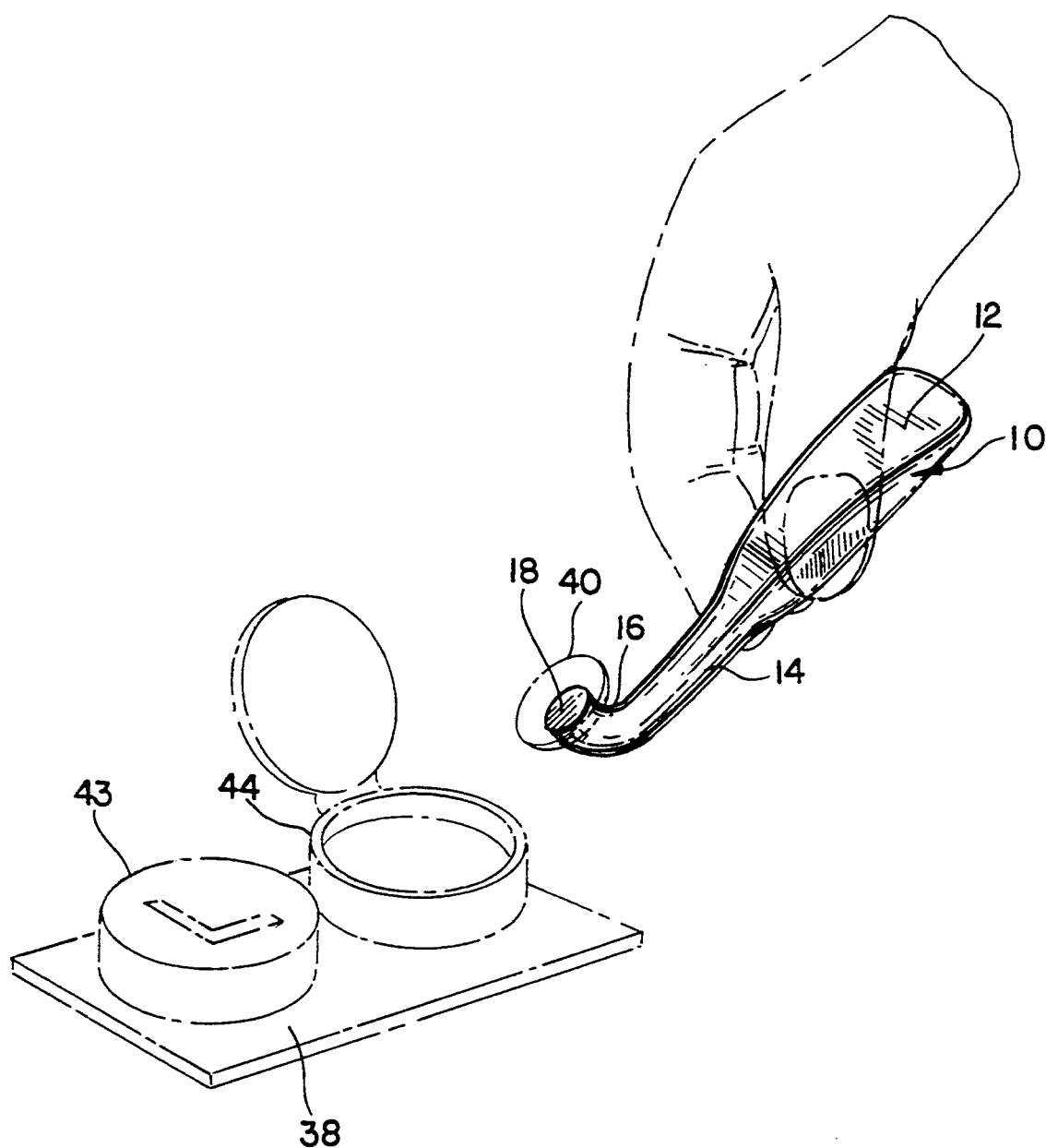
FIG. 8 is a perspective view of adhering a contact lens to the land area of the contact lens insertion tool in accordance with the method of the present invention.
Figure 9:
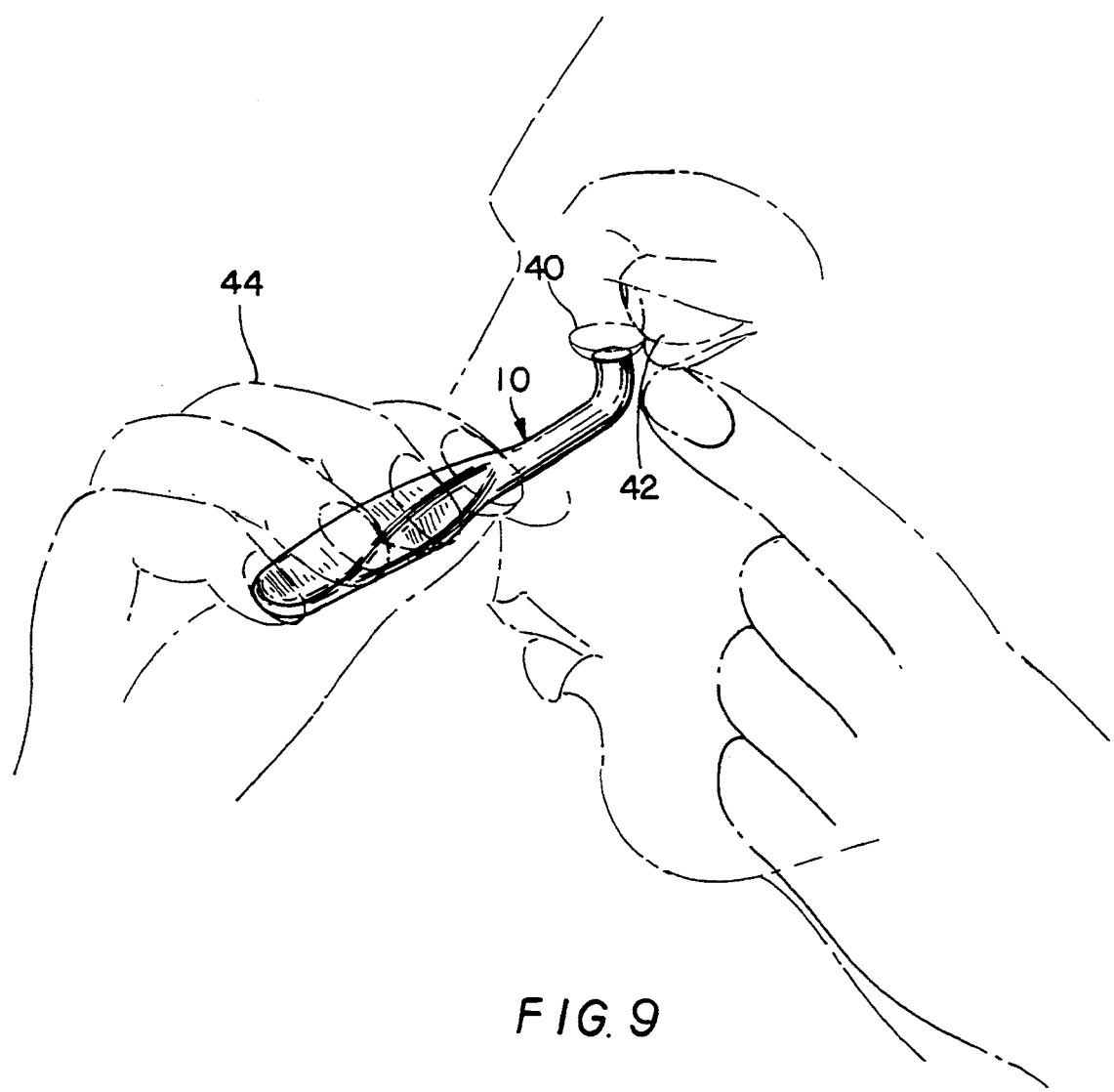
FIG. 9 is a perspective view of the step of depositing a contact lens edge first to the central lower area of the sclera of the eye in accordance with the method of the present invention.

FIGS. 7-11 illustrate the novel steps implemented to insert a contact lens in accordance with the present invention. In FIG. 7, a user's hand 32 is shown picking up contact lens insertion tool 10 from its freely standing position on surface 34. Contact lens insertion tool 10 can be manipulated using only the thumb and the index finger or by all five fingers as shown. Next, as shown in FIG. 8, contact lens insertion tool 10 is used to pick up lens 40 from typical carrying case 38. Contact lens carrying case 38 includes separate compartments 43 and 44 for each of the two lenses. Lens 40 is held in position on land area 18 by the adhesive properties between the contact lens liquid which bathes lens 40 and the surface of land area 18. Referring now to FIG. 9, a right-handed user is shown picking up contact lens insertion tool 10 so that the edge of lens 40 is brought in contact with the bottom central area of the visible sclera 42. It may be necessary for the user to pull down gently on the cheek directly beneath the eyelid with his/her free hand (as shown in FIG. 9) to facilitate contact between the lower sclera 42 and the edge of lens 40. Although FIG. 9 demonstrates one finger pulling down on the cheek directly beneath the eyelid, it may sometimes be necessary to use two fingers to perform this task. It should be noted that when the edge of lens 40 is brought up to the user's eye, that based on the unique angle of contact lens insertion tool 10, neither contact lens insertion tool 10 nor the user's hand 44 impedes the user's vision. The angle of the edge of lens 40 relative to the eye when initial lens edge contact with the eye is made, can range from not greater than 90° to approximately 20° depending upon one's preference.

Figure 10:
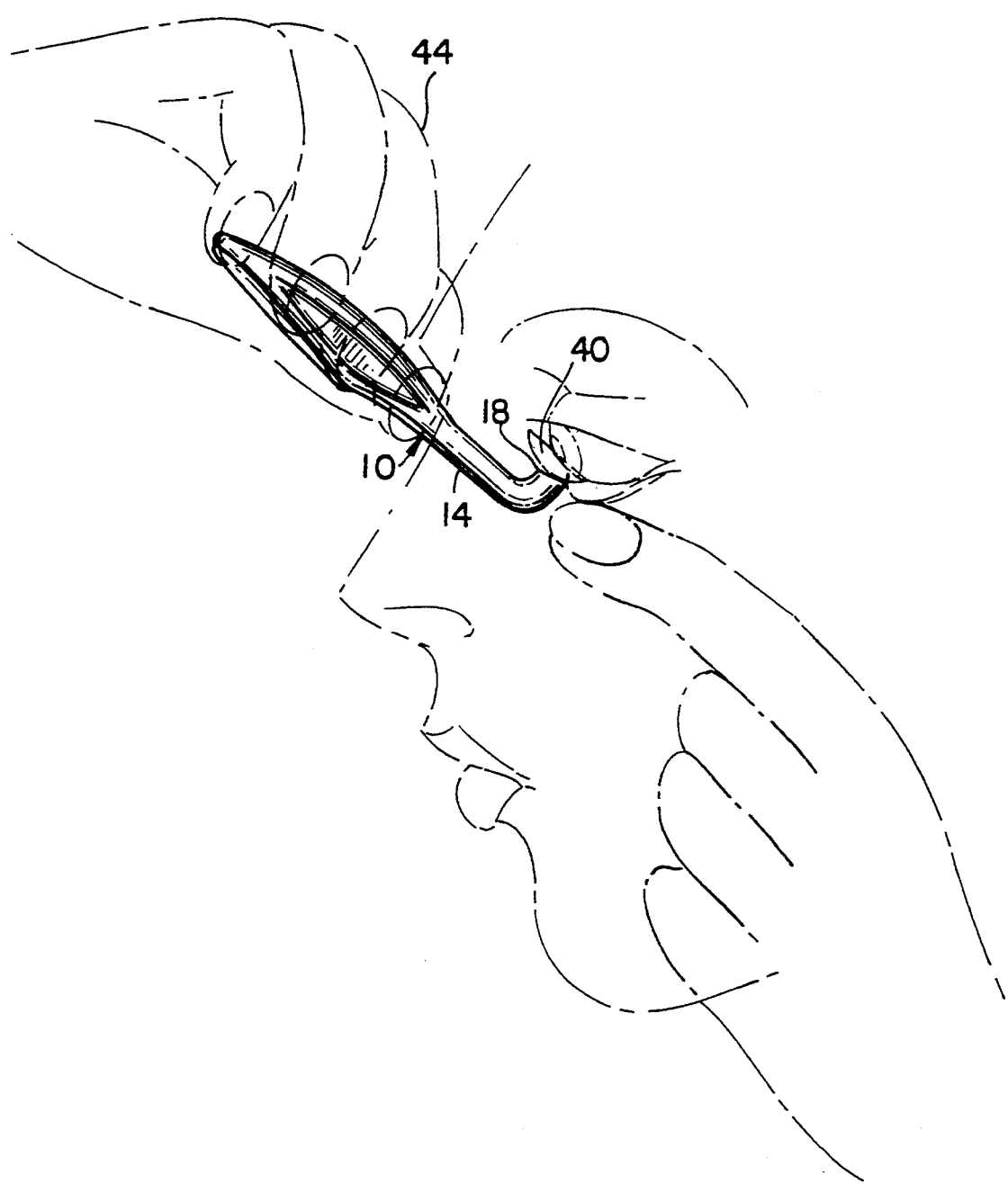
FIG. 10 is a perspective view of the step of rotating the contact lens insertion tool upward so that the contact lens is deposited in the user's eye in accordance with the method of the present invention.

Once the edge of lens 40 is brought in contact with the eye, the user will then rotate contact lens insertion tool 10 upward so that the lens is brought parallel to the eye. This step is shown in FIG. 10. As soon as contact lens insertion tool 10 is rotated to an angular position where the eye-to-lens adhesion exceeds the tool-to-lens adhesion, lens 40 disengages from the inventive contact lens insertion tool 10 and is fully deposited upon the surface of the eye.

Figure 11:
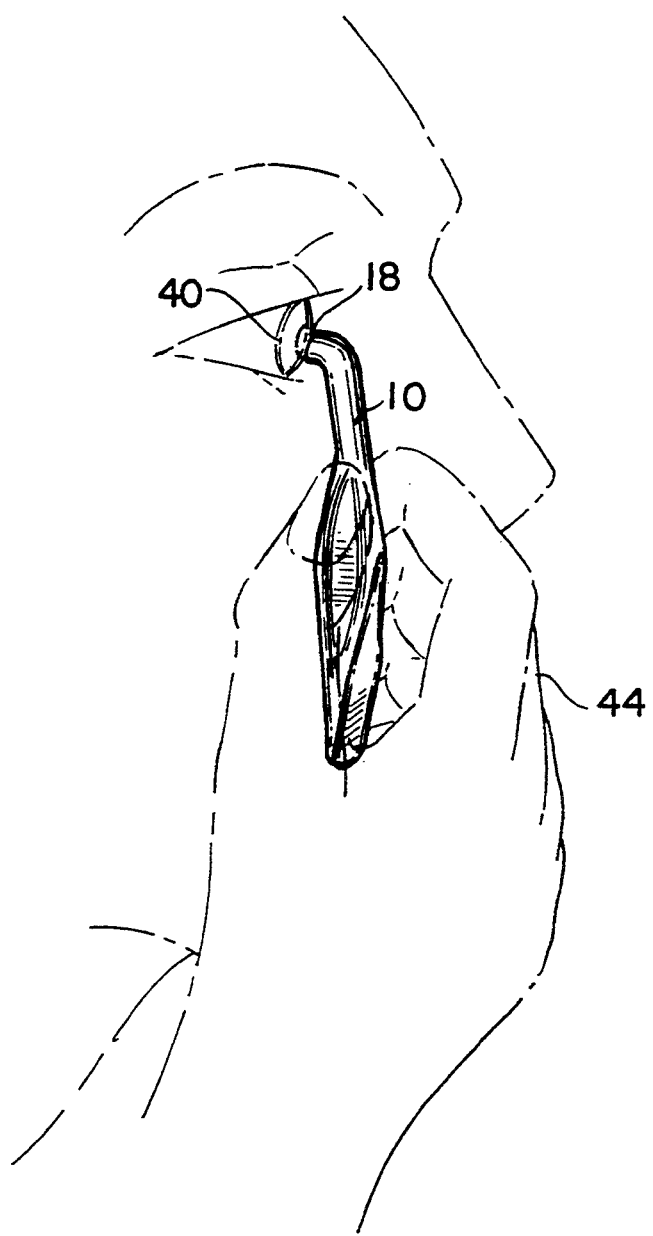
FIG. 11 is a perspective view of the step of manipulating the contact lens insertion tool to align correctly the contact lens over a user's cornea in accordance with the method of the present invention.

Upon inserting the lens into the eye, said lens is often not in the correct position over the cornea. In such instances, lens 40 can be moved into the correct position over the cornea by means of a gentle nudge with contact lens insertion tool 10, as shown in FIG. 11, or by merely blinking a few times.

The contact lens insertion tool and contact lens insertion method described above, substantially reduce the user's need to blink, as the need to blink is greatly increased when an object is brought in close proximity to the upper eyelid. Since the contact lens positioned on the land area of the contact lens insertion tool is brought to the eye at a point on the lower sclera beneath the pupil and the cornea, the line of vision is not impeded, the upper eyelid is not touched, and the tendency to blink is substantially reduced which greatly facilitates the insertion and positioning of said contact lens.

Figure 12:
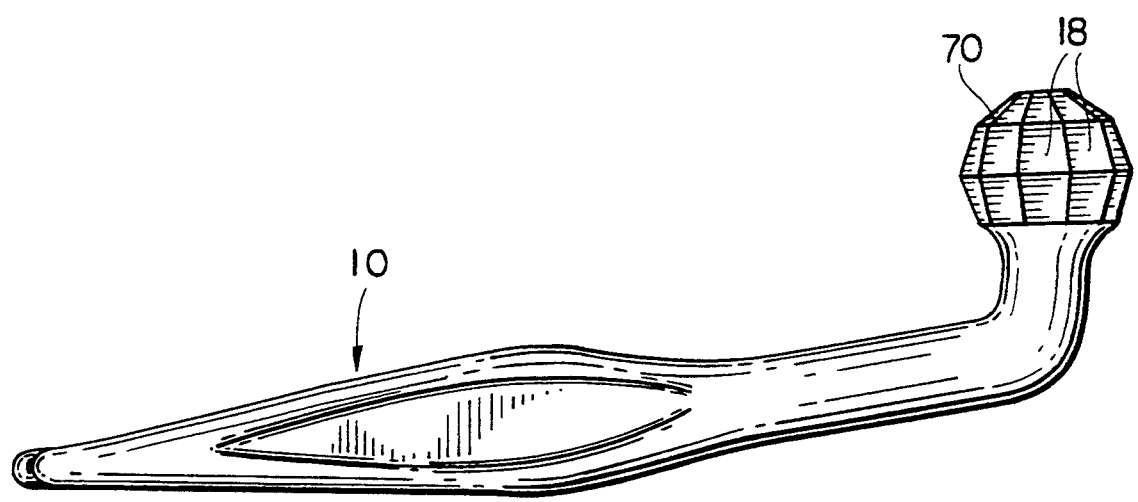
FIG. 12 is a side view of the contact lens insertion tool with faceted ball construction.

Turning now to FIG. 12, the view of the contact lens insertion tool shown in FIG. 2 is repeated, exhibiting a multi-land area configuration embodiment, faceted ball 70. Faceted ball 70, which may have various shapes and textures, allows for numerous regions of contact between the lens 40 and faceted ball 70, depending upon a user's particular preference. When faceted ball 70 is implemented the steps of insertion previously described remain generally the same.

From the foregoing description, it will be apparent that the present invention provides a contact lens insertion tool and method of using the same, which is inexpensive, and which minimizes discomfort and risk of contamination. Moreover, it will be further apparent that the invention provides a contact kens insertion tool which is simple and inexpensive to manufacture.

Various modifications of the invention will occur to those skilled in the art. For example, the angles and external surfaces of the handle section, intermediate section, and the lens supporting section can vary depending upon the size of the user's hand. Furthermore, it will be apparent to those skilled in the art that the inventive contact lens insertion tool and method of implementing the same, can be used for hard, soft, or disposable lenses.

While there have been shown and described what are presently considered to be the preferred embodiments of this invention, it would be obvious to those skilled in the art that various other changes and modifications may be made without departing from the broader aspects of this invention. It is therefore desired that the appended claims cover all such changes and modifications as fall within the true spirit and scope of this invention.

I claim:

1. A tool for viscously engaging a contact lens on a distal end thereof and for placing said contact lens in intimate contact with an eye of a contact lens user, comprising:
   an elongated handle section having a bottom surface;
   said bottom surface having a substantially flat surface along at least a portion of the length thereof;
   an intermediate section angularly displaced from said elongated handle section;
   a lens supporting section angularly displaced from said intermediate section; and
   said handle section enabling said tool to be self-supported in an upright position such that when said bottom surface of said handle section is placed on a flat surface, said lens supporting section is adapted to receive and hold a contact lens thereon.

2. The tool of claim 1 wherein said handle section comprises an essentially flat top surface and narrow side surfaces at a proximal end of said tool, aid opposingly symmetric top and bottom surfaces tapering along a length of said handle section extending away from said proximal end to correspond with the flattening of said side surfaces, whereby said handle section enables said tool to be self-supporting in said upright position when said bottom surface is placed on any flat surface and wherein said user can easily grasp the portion of the side surfaces which are flattened.

3. The tool of claim 2 wherein said intermediate section includes a first end shaped to extend integrally from said handle section and a second end comprising a substantially circular cross section whereby said intermediate section smoothly tapers from its shape at said first end to the substantially circular cross section of said second end.

4. The tool of claim 3 wherein said lens supporting section includes a land area, said land area having a texturized surface adapted to lessen the holding power between the land area and the lens bathed in lens fluid.

5. The tool of claim 3 wherein said lens supporting section includes a land area having a smooth surface adapted to increase the holding power between the land area and the lens bathed in lens fluid.

6. The tool of claim 1 wherein said lens supporting section includes a land area having a smooth flat surface.

7. The tool as claimed in claim 6, wherein the smooth flat surface of the land area is essentially parallel to the essentially flat bottom surface of the handle.

8. The tool of claim 1 wherein aid lens supporting section includes a concave land area.

9. The tool of claim 1 wherein said lens supporting section includes a convex land area.

10. The tool of claim 1 wherein said lens supporting section includes a faceted ball emanating from and integral to said lens supporting section for engaging said contact lens.

11. An integral member tool for inserting a soft contact lens in a user's eye having a top surface, a bottom surface, first and second side surfaces, a distal end and a proximal end, said tool further comprising:
    a handle portion having essentially flat top and bottom surfaces and narrow side surfaces at said proximal end, said opposingly symmetric top and bottom surfaces tapering along a length of said handle portion extending away from said proximal end to correspond with the flattening of said side surfaces, whereby said handle portion enables said tool to be self-supporting in an upright position when said bottom surface is placed on any flat surface and wherein said user can easily grasp the section of side surfaces which are flattened;
    an intermediate portion extending at an obtuse angle from said handle portion including a first end shaped to extend integrally from said handle portion and a second end comprising a substantially circular cross section whereby said intermediate portion smoothly tapers from its configuration at said first end to the substantially circular cross section of said second end;
    a lens supporting portion curving upwardly and integrally from said intermediate portion including a circular land area on said distal end for adhesion between said lens and said tool; and
    said handle portion enabling said tool to be self-supporting in an upright position such that when said bottom surface of the lens handle is placed on a flat surface, said land area is adapted to receive and hold a contact lens thereon.

12. The tool of claim 11 wherein said land area is texturized.

13. The tool of claim 11 wherein said land area is a smooth flat surface.

14. The tool of claim 11 wherein said land area is concave.

15. The tool of claim 11 wherein said land area is convex.

16. The tool of claim 11 further comprising a multi-land area faceted ball configuration for enabling adhesion between said tool and said lens.

17. A method of inserting a moist contact lens in a user's eye, implementing a single member tool having an elongated handle section comprising a top surface, a bottom surface, and two side surfaces, an intermediate section angularly displaced from said handle section, and a lens supporting portion angularly displaced from said intermediate section and further comprising a substantially circular cross sectional land area for engaging said contact lens, said method comprising the steps of:

(a) grasping said handle section of said tool;
(b) adhering said contact lens to said land area by means of the adhesion between the liquid on said lens and the material comprising said land area;
(c) bringing said contact lens edge first to the bottom central area of the sclera of the user's eye into which insertion is desired, and securing contact between said lens edge and the eye at a point on said bottom central sclera area at an angle ranging from approximately 20° to not greater than 90°, in a manner in which said tool does not impede the user's vision in any direction and the necessity to blink is greatly reduced; and
(d) rotating said tool upward toward the eye to an angular position where the adhesion between the contact lens and the eye exceeds the adhesion between the contact lens and the land area of aid tool, whereby said contact lens is disposed in the user's eye.

18. The method of claim 17 further comprising the step of:
(e) gently pulling down on the cheek directly beneath the lower eyelid of the eye to receive said contact lens prior to performing step (c).

19. The method of claim 18 comprising the additional step of:
(f) realigning said contact lens into the correct position over the cornea by means of gently nudging said contact lens with said tool when step (d) fails to provide proper alignment of said contact lens in the user's eye.

20. A method of inserting a moist contact lens in a user's eye, implementing a tool having an elongated handle section and a lens engaging end, said method comprising:
(a) grasping said handle section of said tool;
(b) adhering said contact lens to said lens engaging end by means of the adhesion between the liquid on said lens and said lens engaging end;
(c) bringing said contact lens edge first to the bottom central area of the sclera of the user's eye into which insertion is desired, and securing contact between said lens edge and the eye at a point on said bottom central sclera area at an angle ranging from approximately 20° to not greater than 90° in a manner in which said tool does not impede the user's vision in any direction and the necessity to blink is greatly reduced; and
(d) rotating said tool upward toward the eye to an angular position where the adhesion between the contact lens and the eye exceeds the adhesion between the contact lens and the lens engaging end of said tool, whereby said lens is disposed in the user's eye.

21. The method of claim 20 further comprising the step of:
(e) gently pulling down on the cheek directly beneath the lower eyelid of the eye to receive said contact lens prior to performing step (c).

22. The method of claim 21 comprising the additional step of:
(f) realigning said contact lens into the correct position over the cornea by means of gently nudging said contact lens with said tool when step (d) fails to provide proper alignment of said contact lens in the user's eye.

* * * * *